(12) United States Patent
Gupta et al.

(10) Patent No.: US 8,906,606 B2
(45) Date of Patent: Dec. 9, 2014

(54) METHOD OF PREDICTING AND REDUCING RISK OF METASTASIS OF BREAST CANCER TO LUNG

(75) Inventors: Gaorav P. Gupta, New York, NY (US); Joan Massague, New York, NY (US); Andy J. Minn, New York, NY (US)

(73) Assignee: Sloan-Kettering Institute for Cancer Research, New York, NY (US)

( * ) Notice: Subject to any disclaimer, the term of this patent is extended or adjusted under 35 U.S.C. 154(b) by 0 days.

(21) Appl. No.: 13/447,684

(22) Filed: Apr. 16, 2012

(65) Prior Publication Data

US 2012/0294872 A1 Nov. 22, 2012

Related U.S. Application Data

(62) Division of application No. 11/813,407, filed as application No. PCT/US2006/000461 on Jan. 5, 2006, now Pat. No. 8,178,505.

(60) Provisional application No. 60/641,793, filed on Jan. 5, 2005, provisional application No. 60/702,128, filed on Jul. 25, 2005.

(51) Int. Cl.
*C12Q 1/68* (2006.01)
*C07H 21/04* (2006.01)
*C07H 21/02* (2006.01)

(52) U.S. Cl.
USPC .............................. 435/6; 536/23.1

(58) Field of Classification Search
None
See application file for complete search history.

(56) References Cited

U.S. PATENT DOCUMENTS

2005/0261222 A1 11/2005 Wolber et al.
2006/0025371 A1 2/2006 Trask et al.

OTHER PUBLICATIONS

Bizzarri, C. et al. "ELR+CXC chemokines and their receptors (CXC chemokine receptor 1 and CXC chemokine receptor 2) as new therapeutic targets" Pharmacology & Therapeutics, 2006, pp. 139-149, vol. 112.
Busch-Peterson, J. et al. "Small molecule antagonists of the CXCR2 and CXCR1 chemokine receptors as therapeutic agents for the treatment of inflammatory diseases" Curr. Top Med. Chem. 2006, pp. 135-152, vol. 6, No. 13.
Collins, F. "Generation and initial analysis of more than 15,000 full length human and mouse cDNA sequences" PNAS, Dec. 24, 2002, pp. 16899-16903, vol. 99, No. 26.
Dancey, J. et al. "Epidermal Growth Factor Receptor Inhibitors in Clinical Development" Int. J. Radiation Oncology Biol. Phys., 2004, pp. 1003-1007, vol. 58, No. 3.

Everts, B. et al. "COX-2-Specfic Inhibitors—the Emergence of a New Class of Analgesic and Anti-Inflammatory Drugs" Clinical Rheumatology, 2001, pp. 331-343, vol. 19.
Frolich, J.C. "A classification of NSAIDs according to the relative inhibition of cyclocygenase isoenzymes" TiPS, Jan. 1997, pp. 30-34, vol. 18.
Fujisawa, N. et al. "α-Chemokine growth factors for adenocarcinomas; a synthetic peptide inhibitor for α-chemokines inhibits the growth of adenocarcinoma cell lines" J. Cancer Res. Clin. Oncol., 2000, pp. 19-26, vol. 126.
Kosaka, T. et al. "Characterization of the human gene (PTGS2) encoding prostaglandin-endoperoxide synthase 2" Eur. J. Biochem, 1994, pp. 889-897, vol. 221.
Ohtsuka, T. et al. "Clucocorticoid-mediated Gene Suppression of Rat Cytokine-induced Neutrophil Chemoattractant CINC/gro, a Member of the Interleukin-8 Family, through Impairment of NF-κB Activation" The Journal of Biological Chemistry, 1996, pp. 1651-1659, vol. 271, No. 3.
Schroder, J. et al. "Lipopolysaccharide-Stimulated Human Monocytes Secrete, Apart from Neutrophil-Activating Peptide 1/Interleukin 8, A Second Neutrophil-Activating Protein" J. Exp. Med, Apr. 1990, pp. 1091-1100, vol. 171.
Sekiguchi, T. et al. "Expression of epiregulin and amphiregulin in the rat ovary" Journal of Molecular Endocrinology, 2004, pp. 281-291, vol. 33.
Sirois, Jean et al. "Cyclooxygenase-2 and its role in ovulation:a 2004 account." Human Reproduction Update, Jun. 17, 2004, pp. 373-385, vol. 10, No. 5.
Sirois, J. et al. "Purification and Characterization of a Novel, Distinct Isoform of Prostaglandin Endoperoxide Synthase Induced by Human Chorionic Gonadotropin in Granulosa Cell of Rat Preovulatory Follicles" The Journal of Biological Chemistry, 1992, pp. 6382-6388, vol. 267, No. 9.
Taylor, D. et al. "Epiregulin is a potent vascular smooth muscle cell-derived mitogen induced by angiotension II, endothelin-1, and thrombin" PNAS, Feb. 1999, pp. 1633-1638, vol. 96.
Toyoda, H. et al. "Distribution of mRNA for human epiregulin, a differentially expressed member of the epidermal growth factor family" Biochem. J., 1997, pp. 69-75, vol. 326.
Ushigoe, K. et al. "Production and Regulation of Cytokine-Induced Neutrophil Chemoattractant in Rat Ovulation" Biology of Reproduction, 2000, pp. 121-126, vol. 63.

(Continued)

*Primary Examiner* — Amy Bowman
(74) *Attorney, Agent, or Firm* — Larson & Anderson, LLC

(57) ABSTRACT

A signature for breast cancer tissue derived from a patient is established that is indicative of the virulence and risk of lung metastasis by determining the expression levels to define a sample signature, and comparing this sample signature to a reference signature. This determination is used to define appropriate treatment and monitoring options for the patient. Risk of metastasis to the lung can be reduced by treatment with a therapeutic combination that either (1) contains a first agent effective to inhibit epiregulin activity and a second agent effective to inhibit activity of a protein selected from the group consisting of MMP1, MMP2 and PTGS2, or (2) contains a therapeutic agent or combination of agents effective to inhibit activity MMP1, MMP2 and PTGS2. Agents that inhibit the CXCL1 pathway also can be used individually or in combination with these combinations.

18 Claims, 3 Drawing Sheets

(56) References Cited

OTHER PUBLICATIONS

Wang Haibin et al. "Rescue of Female Infertility from the Loss of Cyclooxygenase-2 by Compensatory Up-regulation of Cyclooxygenase-1 Is a Function of Genetic Makeup." 2004, pp. 10649-10658, vol. 279, No. 11, The Journal of Biological Chemistry.

Watanabe, K. et al. "The Neutrophil Chemoattractant Produced by the Rat Kidney Epithelioid Cell Line NRK-52E is a Protein Related to the KC/gro Protein" The Journal of Biological Chemistry, 1989, pp. 19559-19563, vol. 264, No. 33.

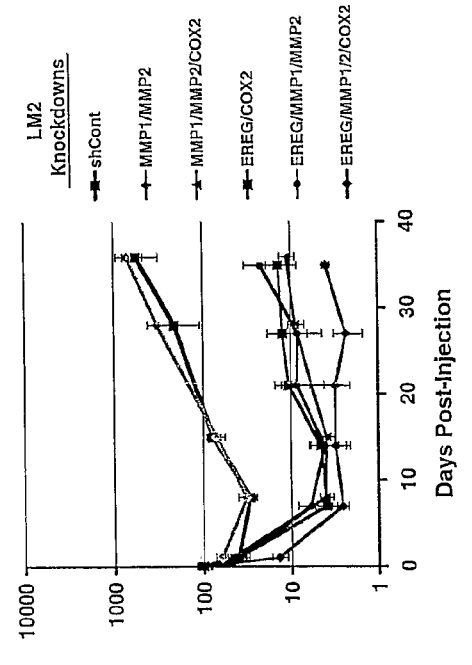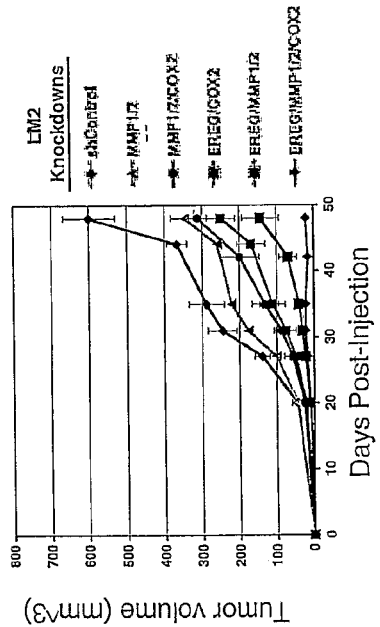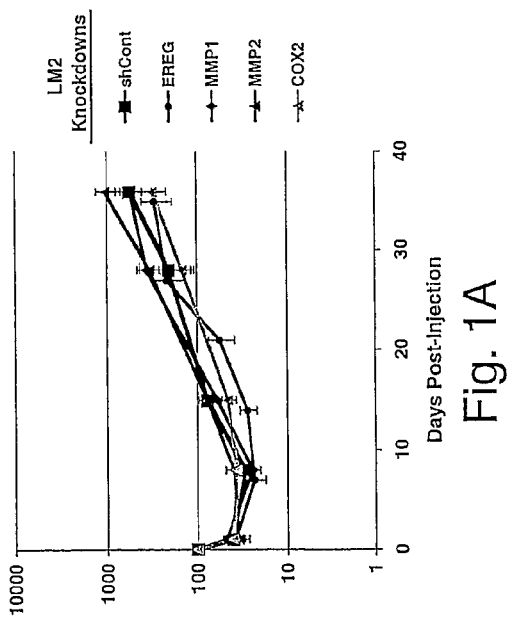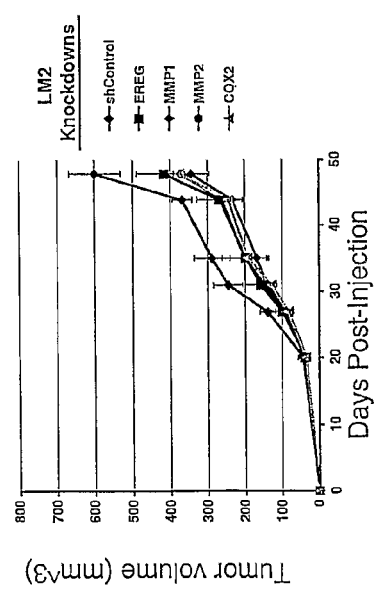

METHOD OF PREDICTING AND REDUCING RISK OF METASTASIS OF BREAST CANCER TO LUNG

STATEMENT OF RELATED APPLICATIONS

This application claims the benefit of U.S. Provisional Applications 60/641,793 filed Jan. 5, 2005 and 60/702,128, filed Jul. 25, 2005, both of which are incorporated herein by reference.

BACKGROUND OF THE INVENTION

This application relates to a method for predicting risk of metastatic breast cancer and to a method of treatment for reducing this risk.

Metastatic breast cancer, either at the time of initial diagnosis or upon recurrence after an initial treatment, commonly occurs in the bone, lung, brain or liver. Between 60% and 70% of women who die from breast cancer have metastatic lung involvement, and in a significant number of cases the lung is the only site of metastasis. The most common signs of lung metastases are: shortness of breath and dry cough. In some cases, women will not experience any symptoms; cancer will only be detected by chest X-ray or CT scan. Thus, the ability to identify early on those cancers that pose the greatest risk of lung metastasis over time would provide an improved prognosis through the use of increased monitoring. Furthermore, the ability to treat metastatic breast cancer that has spread to the lung would decrease the death toll from breast cancer.

SUMMARY OF THE INVENTION

The present application provides a method for establishing a signature for breast cancer tissue derived from a patient that is indicative of the virulence and risk of lung metastasis. In accordance with this aspect of the invention, the expression levels of a plurality of designated genes are evaluated to define a sample signature, and the sample signature is compared to a reference signature. The reference signature defines a standard expression level for each gene and a significant change direction, i.e., either overexpressed or underexpressed. When the expression level in the sample signature differs from the reference signature level for the gene in the significant change direction for a predetermined number of the genes tested, the sample is determined to be one that presents a significant risk of lung metastasis. This determination in turn can be used to define appropriate treatment and monitoring options for the individual patient from whom the sample was obtained.

The invention also provides a therapeutic method for reducing the risk of metastatic breast cancer in a patient previously diagnosed with breast cancer. Applicants have determined that inhibition of certain combinations of therapeutic targets from among the genes tested is effective to reduce the rate of lung metastasis formation. Thus, the invention provides a method for reducing the risk of lung metastases in a patient diagnosed with breast cancer comprising administering to the patient a therapeutic combination comprising
(1) a first agent effective to inhibit epiregulin activity and a second agent effective to inhibit activity of a protein selected from the group consisting of MMP1, MMP2 and PTGS2, or
(2) a therapeutic agent or combination of agents effective to inhibit activity MMP1, MMP2 and PTGS2.

The invention also provides a therapeutic combination comprising a first agent effective to inhibit epiregulin activity and a second agent effective to inhibit activity of a protein selected from the group consisting of MMP1, MMP2 and PTGS2.

The invention also provides a therapeutic combination comprising therapeutic agent(s) effective to inhibit activity MMP1, MMP2 and PTGS2.

BRIEF DESCRIPTION OF THE DRAWINGS

FIGS. 1A-D show the effects of various combinations of RNAi targeting Ereg, MMP1, MMP2, and COX2 on protein expression and tumor volume.

DETAILED DESCRIPTION OF THE INVENTION

Definitions

Figure 2B:
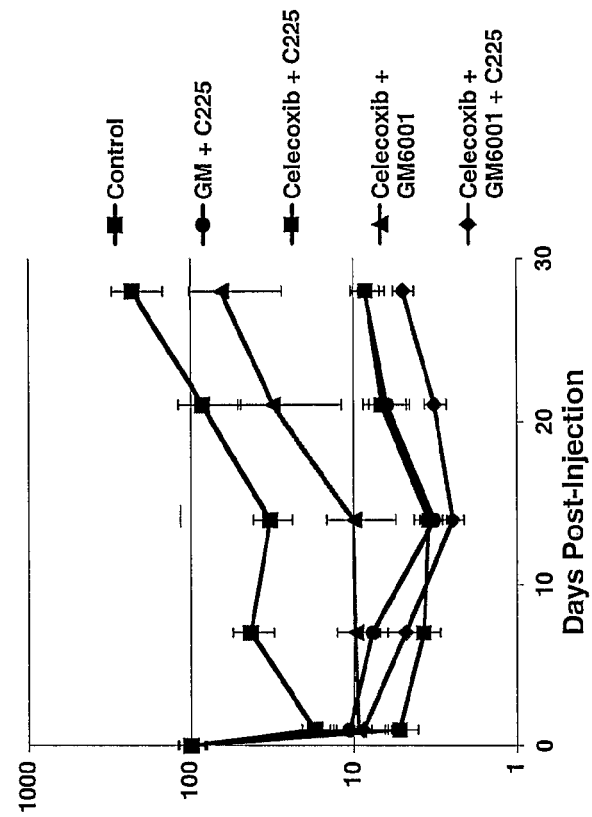
FIGS. 2 A and B show the effects on lung metastasis of pharmacological targeting of Ereg, MMP1, MMP2, and COX2 individually and in various combinations.

As used in the present application, the following definitions should be used in the interpretation of the disclosure and claims:

signature: a set of values for the expression levels of a plurality of genes determined either for a patient-derived tissue sample or established as a reference. The signature provides for each one of the plurality genes an expression level value. In addition, a reference signature provides for each gene an indication of a significant change direction for the gene. The significant change direction indicates whether overexpression or underexpression of the particular protein should be considered significant. As used in the specification and claims of this application, the term "signature" indicates that expression of a sufficient number of gene is tested to obtain a meaningful result with respect to metastatic risk. Persons skilled in the art will appreciate that the number of proteins that must be tested to achieve this result will depend on the statistical significance of the proteins tested. Smaller numbers of genes (for example 10 to 20 genes) with higher statistical significance can be combined to achieve a meaningful result, while larger numbers of proteins may be required if each protein is generally less statistically significant. The results set forth below indicate those proteins found to have the greatest correlation with metastasis.

risk of lung metastases while the present application relates to methods for predicting and/or treating to reduce risk of lung metastases it will be appreciated that no actual proof of reduced risk for an individual can be obtained because if treatment is provided then it cannot be said whether metastases would have occurred, or would have occurred sooner in the absence of such treatment. Thus, the concept of risk and, increased or reduced risk refer to statistical values only. Further, reduction of risk of lung metastasis can be reflected in a reduction in the severity of lung metastasis as well as in the absence of observation or delay in observation of lung metastasis.

expression levels refers to the amount of mRNA encoding a specific protein that is detectable in the sample for each of a plurality of designated genes that are evaluated to define a sample signature or in a reference signature. The reference signature defines a standard expression level for each gene and a significant change direction, i.e., either overexpressed or underexpressed. When the expression level in the sample signature differs from the reference signature level for the gene in the significant change direction for a predetermined number of the genes tested, the sample is determined to be one that presents a significant risk of lung metastasis. This determination in turn can be used to define appropriate treatment and monitoring options for the individual patient from whom the sample was obtained.

therapeutic combination refers to a combination of therapeutic agents that are effective to achieve stated results. The combination may be in the form of a physical mixture (including without limitation true mixture, admixtures and emulsions) or may be a packaged combination of separate agents, preferably packaged in appropriate dosage unit forms. The combination is suitable for administration to human subjects, and thus has appropriate pharmaceutical purity and is free from materials other than the therapeutic agents that create risks of significant toxicity or side effects.

inhibit the activity of a protein refers to any process that results in an effective decrease in protein activity. This can be the result of reduced expression of mRNA encoding the protein, through direct or indirect inhibition of the protein once formed, or through targeted removal/decomposition of a protein. An agent that inhibits is one that inhibits the activity of a protein.

Evaluating Risk of Lung Metastases

In accordance with a first embodiment of the invention, a method is provided for evaluating breast cancer tissue derived from a patient for risk of lung metastases. The first step in this method is obtaining a sample of breast cancer tissue from the patient. The patient will generally be a human patient, and the sample can be obtained using any known means, including without limitation needle biopsy procedures and surgical procedures.

The next step of the method is evaluation of the sample of breast cancer tissue to determine expression levels of a plurality of relevant genes selected from among the 54 genes listed in Table 1. In Table 1, the entry for "Fold Change" is the difference in expression levels between a parental MDA-MB-231 cell and LM2 cells. An entry greater than 1 in the "Fold Change" column is indicative of a upward significant change direction (overexpressed), while a number less than 1 is indicative of a downward significant change direction (underexpressed). The probe set in each case is the number of an Affymetrix™ probe set used for quantitation of the amount expression of the particular gene.

TABLE 1

| Probe set | Fold Change | Gene Title | Gene Symbol |
|---|---|---|---|
| 200665_s_at | 407.01 | secreted protein, acidic, cysteine-rich (osteonectin) | SPARC |
| 212667_at | | | |
| 206172_at | 48.52 | interleukin 13 receptor, alpha 2 | IL13RA2 |
| 206785_s_at | 33.05 | killer cell lectin-like receptor subfamily C, member 1 /// killer cell lectin-like receptor subfamily C, member 2 | KLRC1 /// KLRC2 |
| 204475_at | 13.35 | matrix metalloproteinase 1 (interstitial collagenase) | MMP1 |
| 217388_s_at | 12.82 | kynureninase (L-kynurenine hydrolase) | KYNU |
| 210663_s_at | | | |
| 205767_at | 8.99 | Epiregulin | EREG |
| 201645_at | 7.43 | tenascin C (hexabrachion) | TNC |
| 204698_at | 6.77 | interferon stimulated gene 20 kDa | ISG20 |
| 205623_at | 6.75 | aldehyde dehydrogenase 3 family, memberA1 | ALDH3A1 |
| 213711_at | 6.34 | keratin, hair, basic, 1 | KRTHB1 |
| 204748_at | 6.23 | prostaglandin-endoperoxide synthase 2 (prostaglandin G/H synthase and cyclooxygenase) | PTGS2 |
| 201720_s_at | 5.83 | Lysosomal-associated multispanning membrane protein-5 | LAPTM5 |
| 201721_s_at | | | |
| 203571_s_at | 5.74 | chromosome 10 open reading frame 116, adipose specific 2 | C10orf116 |
| 213194_at | 4.86 | roundabout, axon guidance receptor, homolog 1 (*Drosophila*) | ROBO1 |
| 220217_x_at | 4.56 | SPANX family, member C | SPANXC |
| 221009_s_at | 4.56 | angiopoietin-like 4 | ANGPTL4 |
| 201564_s_at | 4.55 | fascin homolog 1, actin-bundling protein (*Strongylocentrotus purpuratus*) | FSCN1 |
| 210933_s_at | | | |
| 201417_at | 4.45 | SRY (sex determining region Y)-box 4 | SOX4 |
| 201416_at | | | |
| 220922_s_at | 4.4 | SPANX family, member B1 /// SPANX family, member C | SPANXB1 SPANXC |
| 220921_at | | | |
| 213428_s_at | 4.24 | collagen, type VI, alpha 1 | COL6A1 |
| 204470_at | 3.89 | chemokine (C-X-C motif) ligand 1 (melanoma growth stimulating activity, alpha) | CXCL1 |
| 201069_at | 3.85 | matrix metalloproteinase 2 (gelatinase A, 72 kDa gelatinase, 72 kDa type IV collagenase) | MMP2 |
| 201061_s_at | 3.71 | Stomatin | STOM |
| 221902_at | 3.62 | G protein-coupled receptor 153 | GPR153 |
| 221760_at | 3.59 | mannosidase, alpha, class 1A, member 1 | MAN1A1 |
| 219563_at | 3.57 | chromosome 14 open reading frame 139 | C14orf139 |
| 211368_s_at | 3.54 | caspase 1, apoptosis-related cysteine protease (interleukin 1, beta, convertase) | CASP1 |

TABLE 1-continued

| Probe set | Fold Change | Gene Title | Gene Symbol |
|---|---|---|---|
| 209030_s_at | 3.42 | immunoglobulin superfamily, member 4 | IGSF4 |
| 202728_s_at | 3.41 | latent transforming growth factor beta binding protein 1 | LTBP1 |
| 209505_at | 3.24 | nuclear receptor subfamily 2, group F, member 1 | NR2F1 |
| 201325_s_at 201324_at | 3.21 | epithelial membrane protein 1 | EMP1 |
| 208937_s_at | 3.1 | inhibitor of DNA binding 1, dominant negative helix-loop-helix protein | ID1 |
| 222182_s_at | 3.07 | CCR4-NOT transcription complex, subunit 2 | CNOT2 |
| 203868_s_at | 2.17 | vascular cell adhesion molecule 1 | VCAM1 |
| 213075_at | 0.33 | olfactomedin-like 2A | OLFML2A |
| 202149_at | 0.32 | neural precursor cell expressed, developmentally down-regulated 9 | NEDD9 |
| 210340_s_at | 0.32 | colony stimulating factor 2 receptor, alpha, low-affinity (granulocyte-macrophage) | CSF2RA |
| 219959_at | 0.31 | molybdenum cofactor sulfurase | MOCOS |
| 202017_at | 0.3 | epoxide hydrolase 1, microsomal (xenobiotic) | EPHX1 |
| 205018_s_at 205017_s_at | 0.29 | muscleblind-like 2 (*Drosophila*) | MBNL2 |
| 210136_at | 0.25 | LOC388483 | — |
| 214040_s_at | 0.24 | gelsolin (amyloidosis, Finnish type) | GSN |
| 213067_at | 0.24 | myosin, heavy polypeptide 10, non-muscle | MYH10 |
| 202986_at | 0.23 | aryl-hydrocarbon receptor nuclear translocator 2 | ARNT2 |
| 204070_at | 0.21 | retinoic acid receptor responder (tazarotene induced) 3 | RARRES3 |
| 201842_s_at 201843_s_at | 0.21 | EGF-containing fibulin-like extracellular matrix protein 1 | EFEMP1 |
| 202350_s_at | 0.17 | matrilin 2 | MATN2 |
| 202145_at | 0.14 | lymphocyte antigen 6 complex, locus E | LY6E |
| 211991_s_at 213537_at | 0.13 | major histocompatibility complex, class II, DP alpha 1 | HLA-DPA1 |
| 209394_at | 0.1 | acetylserotonin O-methyltransferase-like | ASMTL |
| 208161_s_at | 0.09 | ATP-binding cassette, sub-family C (CFTR/MRP), member 3 | ABCC3 |
| 212942_s_at | 0.07 | KIAA1199 | KIAA1199 |
| 217028_at 209201_x_at | 0.06 | chemokine (C-X-C motif) receptor 4 | CXCR4 |
| 214827_at | 0.04 | par-6 partitioning defective 6 homolog beta (*C. elegans*) | PARD6B |

In a first embodiment of the method of the invention, expression levels of all 54 of the genes listed in Table 1 are evaluated. A breast cancer tissue sample is determined to be one that presents an elevated risk of lung metastasis and a poor patient prognosis if most of the genes, for example 30 or more, more preferably 40 or more, are over or under expressed in a signature pattern consistent with Table 1, when compared to a standard consisting of breast cancer tissue samples from patients that did not develop metastases.

In a second embodiment of a second embodiment of the present invention, the expression levels of a subset of the 54 genes listed in Table 1 are evaluated. For example, one subset of the 54 genes for testing is the 17 genes listed in Table 2. In Table 2, the p value reflects the significance of the correlation between expression level and metastasis. The 17 proteins listed are those found to be most significant. A breast cancer tissue sample is determined to be one that presents an elevated risk of lung metastasis and a poor patient prognosis if most of the 17 genes, for example 10 or more, more preferably 15 or more of the 17 genes are over or under expressed in a signature pattern consistent with Table 1, when compared to a standard consisting of breast cancer tissue samples from patients that did not develop metastases. It will be of course understood that additional genes can be tested for beyond the 17 gene set of Table 2, without departing from the scope of the invention.

TABLE 2

| p-value | UG cluster | Gene symbol | Description |
|---|---|---|---|
| <0.000001 | Hs.118400 | FSCN1 | Fascin homolog 1, actin-bundling protein (*Strongylocentrotus purpuratus*) |
| <0.000001 | Hs.83169 | MMP1 | Matrix metalloproteinase 1 (interstitial collagenase) |
| <0.000001 | Hs.9613 | ANGPTL4 | Angiopoietin-like 4 |
| 0.000006 | Hs.74120 | C10orf116 | Chromosome 10 open reading frame 116 |
| 0.00002 | Hs.789 | CXCL1 | Chemokine (C-X-C motif) ligand 1 (melanoma growth stimulating activity, alpha) |
| 0.000355 | Hs.196384 | PTGS2 | Prostaglandin-endoperoxide synthase 2 (prostaglandin G/H synthase and cyclooxygenase) |
| 0.000444 | Hs.185568 | KRTHB1 | Keratin, hair, basic, 1 |
| 0.000506 | Hs.109225 | VCAM1 | Vascular cell adhesion molecule 1 |
| 0.000627 | Hs.17466 | RARRES3 | Retinoic acid receptor responder (tazarotene induced) 3 |

TABLE 2-continued

| p-value | UG cluster | Gene symbol | Description |
| --- | --- | --- | --- |
| 0.001263 | Hs.368256 | LTBP1 | Latent transforming growth factor beta binding protein 1 |
| 0.004365 | Hs.444471 | KYNU | Kynureninase (L-kynurenine hydrolase) |
| 0.005179 | Hs.421986 | CXCR4 | Chemokine (C-X-C motif) receptor 4 |
| 0.006426 | Hs.77667 | LY6E | Lymphocyte antigen 6 complex, locus E |
| 0.007153 | Hs.410900 | ID1 | Inhibitor of DNA binding 1, dominant negative helix-loop-helix protein |
| 0.010871 | Hs.255149 | MAN1A1 | Mannosidase, alpha, class 1A, member 1 |
| 0.032361 | Hs.388589 | NEDD9 | Neural precursor cell expressed, developmentally down-regulated 9 |
| 0.03713 | Hs.115263 | EREG | Epiregulin |

In a further specific embodiment, the proteins evaluated are the 17 proteins of Table 2, plus Tenascin C (hexabrachion, TNC).

The technique used to perform evaluation of gene expression levels is not critical to the invention, and any known method can be employed provided that the same type of technique is used in determining the numerical standards for the reference signature. Thus, methods that detect mRNA, for example those based on binding of complementary oligonucleotide probes or RNA specific antibodies, and methods that direct expressed protein directly, for example protein specific antibodies or protein specific ligands that are bound by a receptor on the protein, may be used. Exemplary techniques for determination of expression levels include northern blots, RT-PCR, and nucleic Acid microarray techniques and protein immunoaccay and microarray techniques.

If a breast cancer is identified as one that presents an elevated risk for lung metastasis, several steps in the treatment/monitoring process for the individual patient are indicated:

(1) more aggressive treatment in the first instance because the tumor is a high risk tumor;

(2) more frequent follow-ups, with a focus on diagnostic imaging procedures in the lung.

The invention also provides a therapeutic method for reducing the risk of metastatic breast cancer in a patient previously diagnosed with breast cancer. Applicants have determined that inhibition of certain combinations of therapeutic targets from among the genes tested is effective to reduce the rate of lung metastasis formation. Thus, the invention provides a method for reducing the risk of lung metastases in a patient diagnosed with breast cancer comprising administering to the patient a therapeutic combination comprising (1) a first agent effective to inhibit epiregulin activity and a second agent effective to inhibit activity of a protein selected from the group consisting of MMP1, MMP2 and PTGS2, or (2) a therapeutic agent or combination of agents effective to inhibit activity MMP1, MMP2 and PTGS2.

The invention also provides a therapeutic combination comprising a first agent effective to inhibit epiregulin activity and a second agent effective to inhibit activity of a protein selected from the group consisting of MMP1, MMP2 and PTGS2.

The invention also provides a therapeutic combination comprising therapeutic agent(s) effective to inhibit activity MMP1, MMP2 and PTGS2.

Suitable therapeutic agents may be RNAi or other oligonucleotide (for example antisense) targeted against these and other genes or protein-targeted inhibitory compounds, for example antibodies or binding ligands, against extracellular proteins within the marker protein set can be used as therapeutic agents. Administration of these agents in appropriate carriers known in the art, and in amounts determined to be therapeutically effective is within the skill in the art. Oligonucleotides can also be administered in the form of vectors that lead to the production (expression) of inhibitory oligonucleotide in situ.

Therapies for Epiregulin (also known as EREG, an EGFR/HER receptor family ligand) are those targeting the EGF receptor, including Erbitux, Iressa and Tarceva, and those against HER2, which is currently Herceptin.

PTGS2, also known as COX2, has several known inhibitors already approved and in the market. Among them there is Vioxx (rofecoxib, Merck) and its second generation version Arcoxia, and Celebrex (celocoxib) and its second generation version Bextra (valdecoxib) (Pfizer), Indocin, or not yet approved Pharmacia parecoxib. There are also other drugs that inhibit Cox2 that can be used, although they have lower selectivity, since they also inhibit Cox1, among them are aspirin, Advil, Aleve, naproxen and ibuprofen.

MMP1 and MMP2 can be inhibited with several compounds that are currently undergoing clinical trials. Among them there is Marimastat (BB-2516) and its analog Batimastat (BB-94), both are synthetic, low-molecular weight compounds. Other drugs are: AG3340 (Agouron) which is now in a phase III tria; 12-9566 (Bayer Corporation); D2163 (Chiroscience Group Plc); Metastat, also known as COL-3 (Collagenex) and MMI270 (Novartis). Some of these drugs have been reported to present difficulties for routine therapeutic use, however the risks posed by these agents would be very tolerable in the context of treating metastatic disease, which is often fatal. Also, recently it has been found that an old class of antibiotics, the tetracyclines, acts as broad-spectrum MMP inhibitors. Collagenex's Periostat. Bryostatins, naturally occurring macrocyclic lactones, have both in vitro and in vivo activity in numerous murine and human tumors. In culture, bryostatin-1 has been shown to induce differentiation and halt the growth of several malignant cell lines. While the exact mechanism responsible for anti-tumor activity is unclear, an initial event in the action of bryostatin-1 is activation of protein kinase C (PKC), followed by its down regulation. Bryostatin-1 does not directly affect the activity of MMPs, but it can inhibit the production of MMP-1, 3, 9, 10 and 11 by inhibiting PKC. Applicants have also found that targeted inhibition of the CXCL1 chemokine pathway, either individually or in combination with the aforementioned therapies, provides an effective therapeutic combination to inhibit lung metastasis. Inhibition of the CXCL1 pathway can be achieved either by directly targeting the ligand or by inhibition of its cognate receptor, CXCR2. Several experimental agents targeting this pathway are being developed for clinical use, including SB-332235 and SB-265610, both of which are produced by GlaxoSmithKline. Several agents targeting this pathway have already begun phase I clinical trials for efficacy against inflammatory diseases, and our results suggest that they may also be useful as anti-metastasis therapies for cancer patients. Thus, the therapeutic compositions of the invention may further comprise an agent effective to inhibit the CXCL1 pathway.

Experimental Evidence in Support of Invention

The following description of the experiments leading the discovery of the present invention is provided by way of non-limiting example.

The identity and time of onset of the changes that endow tumor cells with these metastatic functions are largely unknown and the subject of debate. It is believed that genomic instability generates large-scale cellular heterogeneity within tumor populations, from which rare cellular variants with augmented metastatic abilities evolve through a Darwinian selection process. (Fidler, I. J. The pathogenesis of cancer metastasis: the 'seed and soil' hypothesis revisited. Nat Rev Cancer 3, 453-8 (2003); Yokota, J. Tumor progression and metastasis. Carcinogenesis 21, 497-503 (2000).) Work on experimental metastasis using tumor cell lines has demonstrated that re-injection of metastatic cell populations can enrich for the metastatic phenotype.) Kang, Y. et al. A multigenic program mediating breast cancer metastasis to bone. Cancer Cell 3, 537-49 (2003); Clark, E. A., Golub, T. R., Lander, E. S. & Hynes, R. O. Genomic analysis of metastasis reveals an essential role for RhoC. Nature 406, 532-5 (2000); Yang, J. et al. Twist, a master regulator of morphogenesis, plays an essential role in tumor metastasis. Cell 117, 927-39 (2004).)

Recently, however, the existence of genes that specifically mediate metastasis by rare cellular variants has been challenged. (Bernards, R. & Weinberg, R. A. A progression puzzle. Nature 418, 823 (2002).) Transcriptomic profiling of primary human carcinomas have identified gene expression patterns which, when present in the bulk primary tumor population, predict poor patient prognosis. (van de Vijver, M. J. et al. A gene-expression signature as a predictor of survival in breast cancer. N Engl J Med 347, 1999-2009 (2002); van't Veer, L. J. et al. Gene expression profiling predicts clinical outcome of breast cancer. Nature 415, 530-6 (2002); Ramaswamy, S., Ross, K. N., Lander, E. S. & Golub, T. R. A molecular signature of metastasis in primary solid tumors. Nat Genet 33, 49-54 (2003).) The existence of such signatures has been interpreted to mean that genetic lesions acquired early in tumorigenesis are sufficient for the metastatic process, and that consequently no metastasis-specific genes may exist. (Bernards (2002) supra) However, it is unclear whether these genes that predict metastatic recurrence are also functional mediators.

The lungs and bones are frequent sites of breast cancer metastasis, and metastases to these sites differ in terms of their evolution, treatment, morbidity and mortality. (Solomayer, E. F., Diel, I. J., Meyberg, G. C., Gollan, C. & Bastert, G. Metastatic breast cancer: clinical course, prognosis and therapy related to the first site of metastasis. Breast Cancer Res Treat 59, 271-8 (2000).) The present inventors reasoned that each organ site places different demands on circulating cancer cells for the establishment of metastases, and sought to identify genes whose expression in breast cancer cells confers functions necessary for lung metastasis. By combining in vivo selection for lung metastatic cells, transcriptomic profiling and functional testing, we have identified genes that selectively mediate lung metastasis and correlate with the propensity of primary human breast cancers to relapse to the lung.

The cell line MDA-MB-231 used in the experiments described herein was derived from the pleural effusion of a breast cancer patient suffering from widespread metastasis years after removal of her primary tumor. (Cailleau, R., Olive, M. & Cruciger, Q. V. Long-term human breast carcinoma cell lines of metastatic origin: preliminary characterization. In Vitro 14, 911-5 (1978).) Individual MDA-MB-231 cells grown and tested as single cell-derived progenies (SCPs) exhibit distinct metastatic ability and tissue tropism (van't Veer (2002) supra) despite having similar expression levels of genes constituting a validated Rosetta-type poor prognosis signature. (Minn, A. J. et al. Distinct organ-specific metastatic potential of individual breast cancer cells and primary tumors. J Clin Invest 115, 44-55 (2005).) However, differences in the overall gene expression pattern of these SCPs allow their unsupervised classification into three groups. Because each of these groups displays a distinct ability to metastasize to lung or bone, we hypothesized that some of the genes differentially expressed in these SCPs determine organ-specific metastasis. Indeed, previous work has demonstrated that most of the genes linked to the activity of bone metastatic subpopulations are among those that are differentially expressed between the three SCP groups.

To identify genes that mediate lung metastasis we tested parental MDA-MB-231 cells and the 1834 sub-line (an in vivo isolate with no enhancement in bone metastatic behavior) by tail vein injection into immunodeficient mice. Metastatic activity was assayed using bioluminescence imaging of luciferase-transduced cells as well as gross examination of the lungs at necropsy. The 1834 cells exhibited limited but significant lung metastatic activity compared to the parental population. When 1834-derived lung lesions were expanded in culture and re-inoculated into mice, these cells (denoted as LM1 subpopulations) exhibited increased lung metastatic activity. Another round of in vivo selection yielded second-generation populations (denoted LM2) that were rapidly and efficiently metastatic to lung. Histological analysis confirmed that LM2 lesions replaced large areas of the lung parenchyma, whereas 1834 cells exhibited intravascular growth with less extensive extravasation and parenchymal involvement. Inoculation of as few as $2 \times 10^3$ LM2 cells was sufficient for the emergence of aggressive lung metastases whereas inoculation of $2 \times 10^5$ parental cells left only a residual, indolent population in the lungs. Furthermore, the enhancement in lung metastatic activity was tissue-specific. When LM2 populations were inoculated into the left cardiac ventricle to facilitate bone metastasis, their metastatic activity was comparable to that of the parental and 1834 populations, and it was markedly inferior to that of a previously described, highly aggressive bone metastatic population.

To identify patterns of gene expression associated with aggressive lung metastatic behavior, we performed transcriptomic microarray analysis of the highly and weakly lung metastatic cell populations. The gene list obtained from a class comparison between parental and LM2 populations was filtered to exclude genes that were expressed at low levels in a majority of samples and to ensure a 3-fold or higher change in expression level between the two groups. A total of 95 unique genes (113 probe sets) met these criteria with 48 overexpressed and 47 underexpressed in cell populations most metastatic to the lung. These genes and their expression levels are listed in Table 3.

TABLE 3

| Probe set | Fold Change | Gene Title | Gene Symbol |
|---|---|---|---|
| 200665_s_at | 407.01 | secreted protein, acidic, cysteine-rich (osteonectin) | SPARC |
| 203029_s_at | 147.27 | protein tyrosine phosphatase, receptor type, N polypeptide 2 | PTPRN2 |
| 203030_s_at | 97.07 | protein tyrosine phosphatase, receptor type, N polypeptide 2 | PTPRN2 |
| 207442_at | 58.71 | colony stimulating factor 3 (granulocyte) | CSF3 |
| 206172_at | 48.52 | interleukin 13 receptor, alpha 2 | IL13RA2 |
| 206785_s_at | 33.05 | killer cell lectin-like receptor subfamily C, member 1 /// killer cell lectin-like receptor subfamily C, member 2 | KLRC1 /// KLRC2 |
| 202310_s_at | 20.03 | collagen, type I, alpha 1 | COL1A1 |
| 211534_x_at | 15.67 | protein tyrosine phosphatase, receptor type, N polypeptide 2 | PTPRN2 |
| 221261_x_at | 14.65 | melanoma antigen, family D, 4 /// melanoma antigen, family D, 4 | MAGED4 |
| 202947_s_at | 13.5 | glycophorin C (Gerbich blood group) | GYPC |
| 204475_at | 13.35 | matrix metalloproteinase 1 (interstitial collagenase) | MMP1 |
| 217388_s_at | 12.82 | kynureninase (L-kynurenine hydrolase) | KYNU |
| 205767_at | 8.99 | Epiregulin | EREG |
| 201645_at | 7.43 | tenascin C (hexabrachion) | TNC |
| 204698_at | 6.77 | Interferon stimulated gene 20 kDa | ISG20 |
| 205623_at | 6.75 | Aldehyde dehydrogenase 3 family, memberA1 | ALDH3A1 |
| 212091_s_at | 6.35 | collagen, type VI, alpha 1 | COL6A1 |
| 213711_at | 6.34 | keratin, hair, basic, 1 | KRTHB1 |
| 210663_s_at | 6.29 | kynureninase (L-kynurenine hydrolase) | KYNU |
| 204748_at | 6.23 | prostaglandin-endoperoxide synthase 2 (prostaglandin G/H synthase and cyclooxygenase) | PTGS2 |
| 201720_s_at | 5.83 | Lysosomal-associated multispanning membrane protein-5 | LAPTM5 |
| 203571_s_at | 5.74 | chromosome 10 open reading frame 116, adipose specific 2 | C10ORF116 |
| 204205_at | 5.29 | apolipoprotein B mRNA editing enzyme, catalytic polypeptide-like 3G | APOBEC3G |
| 205463_s_at | 5.02 | platelet-derived growth factor alpha polypeptide | PDGFA |
| 213194_at | 4.86 | roundabout, axon guidance receptor, homolog 1 (Drosophila) | ROBO1 |
| 212190_at | 4.63 | serine (or cysteine) proteinase inhibitor, clade E (nexin, plasminogen activator inhibitor type 1), member 2 | SERPINE2 |
| 220217_x_at | 4.56 | SPANX family, member C | SPANXC |
| 221009_s_at | 4.56 | angiopoietin-like 4 | ANGPTL4 |
| 201564_s_at | 4.55 | fascin homolog 1, actin-bundling protein (Strongylocentrotus purpuratus) | FSCN1 |
| 216268_s_at | 4.47 | jagged 1 (Alagille syndrome) | JAG1 |
| 201417_at | 4.45 | SRY (sex determining region Y)-box 4 | SOX4 |
| 220922_s_at | 4.4 | SPANX family, member B1 /// SPANX family, member C | SPANXB1 /// SPANXC |
| 201288_at | 4.26 | Rho GDP dissociation inhibitor (GDI) beta | ARHGDIB |
| 213428_s_at | 4.24 | collagen, type VI, alpha 1 | COL6A1 |
| 220921_at | 4.21 | SPANX family, member B1 | SPANXB1 |
| 33304_at | 4.16 | Interferon stimulated gene 20 kDa | ISG20 |
| 205174_s_at | 4.01 | glutaminyl-peptide cyclotransferase (glutaminyl cyclase) | QPCT |
| 210933_s_at | 3.99 | fascin homolog 1, actin-bundling protein (Strongylocentrotus purpuratus) | FSCN1 |
| 204470_at | 3.89 | chemokine (C-X-C motif) ligand 1 (melanoma growth stimulating activity, alpha) | CXCL1 |
| 201069_at | 3.85 | matrix metalloproteinase 2 (gelatinase A, 72 kDa gelatinase, 72 kDa type IV collagenase) | MMP2 |

TABLE 3-continued

| Probe set | Fold Change | Gene Title | Gene Symbol |
|---|---|---|---|
| 205399_at | 3.76 | doublecortin and CaM kinase-like 1 | DCAMKL1 |
| 201061_s_at | 3.71 | Stomatin | STOM |
| 221902_at | 3.62 | G protein-coupled receptor 153 | GPR153 |
| 221760_at | 3.59 | mannosidase, alpha, class 1A, member 1 | MAN1A1 |
| 219563_at | 3.57 | chromosome 14 open reading frame 139 | C14orf139 |
| 211368_s_at | 3.54 | caspase 1, apoptosis-related cysteine protease (interleukin 1, beta, convertase) | CASP1 |
| 209030_s_at | 3.42 | immunoglobulin superfamily, member 4 | IGSF4 |
| 202728_s_at | 3.41 | latent transforming growth factor beta binding protein 1 | LTBP1 |
| 204385_at | 3.24 | kynureninase (L-kynurenine hydrolase) | KYNU |
| 209505_at | 3.24 | nuclear receptor subfamily 2, group F, member 1 | NR2F1 |
| 201325_s_at | 3.21 | epithelial membrane protein 1 | EMP1 |
| 201721_s_at | 3.21 | Lysosomal-associated multispanning membrane protein-5 | LAPTM5 |
| 206097_at | 3.17 | solute carrier family 22 (organic cation transporter), member 1-like antisense | SLC22A1LS |
| 201324_at | 3.15 | epithelial membrane protein 1 | EMP1 |
| 203417_at | 3.12 | microfibrillar-associated protein 2 | MFAP2 |
| 208937_s_at | 3.1 | inhibitor of DNA binding 1, dominant negative helix-loop-helix protein | ID1 |
| 219911_s_at | 3.1 | solute carrier organic anion transporter family, member 4A1 | SLCO4A1 |
| 222182_s_at | 3.07 | CCR4-NOT transcription complex, subunit 2 | CNOT2 |
| 222103_at | 3.07 | Activating transcription factor 1 | ATF1 |
| 203585_at | 3.06 | zinc finger protein 185 (LIM domain) | ZNF185 |
| 221911_at | 3.02 | hypothetical protein LOC221810 | LOC221810 |
| 216488_s_at | 0.33 | ATPase, Class VI, type 11A | ATP11A |
| 205017_s_at | 0.33 | muscleblind-like 2 (Drosophila) | MBNL2 |
| 210046_s_at | 0.33 | isocitrate dehydrogenase 2 (NADP+), mitochondrial | IDH2 |
| 213075_at | 0.33 | olfactomedin-like 2A | OLFML2A |
| 202149_at | 0.32 | neural precursor cell expressed, developmentally down-regulated 9 | NEDD9 |
| 202610_s_at | 0.32 | cofactor required for Sp1 transcriptional activation, subunit 2, 150 kDa | CRSP2 |
| 210340_s_at | 0.32 | colony stimulating factor 2 receptor, alpha, low-affinity (granulocyte-macrophage) | CSF2RA |
| 221011_s_at | 0.32 | likely ortholog of mouse limb-bud and heart gene /// likely ortholog of mouse limb-bud and heart gene | LBH |
| 219959_at | 0.31 | molybdenum cofactor sulfurase | MOCOS |
| 213537_at | 0.31 | major histocompatibility complex, class II, DP alpha 1 | HLA-DPA1 |
| 202237_at | 0.3 | nicotinamide N-methyltransferase | NNMT |
| 206473_at | 0.3 | membrane-bound transcription factor protease, site 2 | MBTPS2 |
| 201428_at | 0.3 | claudin 4 | CLDN4 |
| 201843_s_at | 0.3 | EGF-containing fibulin-like extracellular matrix protein 1 | EFEMP1 |
| 202017_at | 0.3 | epoxide hydrolase 1, microsomal (xenobiotic) | EPHX1 |
| 202688_at | 0.3 | tumor necrosis factor (ligand) superfamily, member 10 | TNFSF10 |
| 205018_s_at | 0.29 | muscleblind-like 2 (Drosophila) | MBNL2 |
| 203387_s_at | 0.29 | TBC1 domain family, member 4 | TBC1D4 |
| 212372_at | 0.28 | myosin, heavy polypeptide 10, non-muscle | MYH10 |
| 205805_s_at | 0.27 | receptor tyrosine kinase-like orphan receptor 1 | ROR1 |
| 216060_s_at | 0.27 | dishevelled associated activator of morphogenesis 1 | DAAM1 |
| 203974_at | 0.26 | haloacid dehalogenase-like hydrolase domain containing 1A | HDHD1A |
| 204149_s_at | 0.25 | glutathione S-transferase M4 | GSTM4 |
| 210136_at | 0.25 | LOC388483 | — |
| 214040_s_at | 0.24 | gelsolin (amyloidosis, Finnish type) | GSN |

TABLE 3-continued

| Probe set | Fold Change | Gene Title | Gene Symbol |
|---|---|---|---|
| 213067_at | 0.24 | myosin, heavy polypeptide 10, non-muscle | MYH10 |
| 207379_at | 0.24 | EGF-like repeats and discoidin I-like domains 3 | EDIL3 |
| 201137_s_at | 0.23 | major histocompatibility complex, class II, DP beta 1 | HLA-DPB1 |
| 208306_x_at | 0.23 | major histocompatibility complex, class II, DR beta 3 | HLA-DRB3 |
| 215193_x_at | 0.23 | major histocompatibility complex, class II, DR beta 3 | HLA-DRB3 |
| 202986_at | 0.23 | aryl-hydrocarbon receptor nuclear translocator 2 | ARNT2 |
| 206814_at | 0.22 | nerve growth factor, beta polypeptide | NGFB |
| 204070_at | 0.21 | retinoic acid receptor responder (tazarotene induced) 3 | RARRES3 |
| 202238_s_at | 0.21 | nicotinamide N-methyltransferase | NNMT |
| 201842_s_at | 0.21 | EGF-containing fibulin-like extracellular matrix protein 1 | EFEMP1 |
| 207620_s_at | 0.18 | calcium/calmodulin-dependent serine protein kinase (MAGUK family) | CASK |
| 211990_at | 0.18 | Major histocompatibility complex, class II, DP alpha 1 | — |
| 202350_s_at | 0.17 | matrilin 2 | MATN2 |
| 211907_s_at | 0.16 | par-6 partitioning defective 6 homolog beta (*C. elegans*) /// par-6 partitioning defective 6 homolog beta (*C. elegans*) | PARD6B |
| 207214_at | 0.16 | serine protease inhibitor, Kazal type 4 | SPINK4 |
| 211839_s_at | 0.16 | colony stimulating factor 1 (macrophage) | CSF1 |
| 208209_s_at | 0.16 | complement component 4 binding protein, beta | C4BPB |
| 202145_at | 0.14 | lymphocyte antigen 6 complex, locus E | LY6E |
| 211991_s_at | 0.13 | major histocompatibility complex, class II, DP alpha 1 | HLA-DPA1 |
| 204238_s_at | 0.12 | chromosome 6 open reading frame 108 | C6orf108 |
| 209394_at | 0.1 | acetylserotonin O-methyltransferase-like | ASMTL |
| 208161_s_at | 0.09 | ATP-binding cassette, sub-family C (CFTR/MRP), member 3 | ABCC3 |
| 209201_x_at | 0.08 | chemokine (C-X-C motif) receptor 4 | CXCR4 |
| 210140_at | 0.07 | cystatin F (leukocystatin) | CST7 |
| 212942_s_at | 0.07 | KIAA1199 | KIAA1199 |
| 217028_at | 0.06 | chemokine (C-X-C motif) receptor 4 | CXCR4 |
| 214827_at | 0.04 | par-6 partitioning defective 6 homolog beta (*C. elegans*) | PARD6B |

This gene set was largely distinct from the bone metastasis gene-expression signature previously identified in bone metastatic isolates derived from the same cell line. In fact, only 6 genes overlapped with concordant expression patterns between the two groups as listed in Table 4.

TABLE 4

| Probe set | Description | Gene symbol | Bone | Lung |
|---|---|---|---|---|
| 201417_at | SRY (sex determining region Y)-box 4 | SOX4 | down | up |
| 203571_s_at | adipose specific 2 | C10orf116 | down | Up |
| 208161_s_at | ATP-binding cassette, sub-family C (CFTR/MRP), 3 | ABCC3 | down | Down |
| 211991_s_at | major histocompatibility complex, class II, DP alpha 1 | HLA-DPA1 | down | Down |
| 219563_at | chromosome 14 open reading frame 139 | C14orf139 | up | Up |
| 204475_at | matrix metalloproteinase 1 (interstitial collagenase) | MMP1 | up | Up |
| 209201_x_at | Chemokine (C-X-C motif) receptor 4 | CXCR4 | up | Down |
| 220921_at | sperm protein associated with the nucleus, X chromosome, family member A1 | SPANXA1 | up | Up |
| 220922_s_at | sperm protein associated with the nucleus, X chromosome, family member A1 | SPANXA1 | up | Up |
| 215193_x_at | major histocompatibility complex, class II, DR beta 1 | HLA-DRB1 | down | Down |

TABLE 4-continued

| Probe set | Description | Gene symbol | Bone | Lung |
|---|---|---|---|---|
| 201137_s_at | major histocompatibility complex, class II, DP beta 1 | HLA-DPB1 | down | Down |

Hierarchical clustering with the 95-gene list confirmed a robust relationship between this gene-expression signature and the lung-specific metastatic activity of in vivo-selected cell populations. In addition, this gene expression signature segregated the SCPs (which were not used in generation of the gene list) into two major groups, one transcriptomically resembling the parental cells, and the other more similar to the in vivo-selected lung metastatic populations. This latter group of SCPs was also more metastatic to lung than the former group. However, unlike the LM2 populations, none of the SCPs expressed the complete gene expression signature. Consistent with this observation, the lung metastatic activity of the LM2 populations was approximately one order of magnitude greater than the most aggressive SCPs. We postulated that the subset of genes from the 95-gene signature that are uniformly expressed by all lung metastatic SCPs and in vivo-selected populations may confer baseline lung metastatic functions, which we define as lung metastagenicity. Genes that are expressed exclusively in the most aggressive LM2 populations may serve specialized, lung-restricted functions, which we collectively denote as lung metastatic virulence. A final list of 54 candidate lung metastagenicity and virulence genes was selected for further evaluation (Table 1).

A subset of biologically intriguing genes overexpressed in the 54 gene list was selected for functional validation. These genes include the EGF family member epiregulin (EREG), which is a broad-specificity ligand for the HER/ErbB family of receptors, the chemokine GRO1/CXCL1, the matrix metalloproteinases MMP1 (collagenase 1) and MMP2 (gelatinase A), the cell adhesion molecule SPARC19, the interleukin-13 decoy receptor IL13R 2 and the cell adhesion receptor VCAM1. These genes encode secretory or receptor proteins, suggesting roles in the tumor cell microenvironment. In addition to these genes, we also included the transcriptional inhibitor of cell differentiation and senescence ID1 and the prostaglandin-endoperoxide synthase PTGS2/COX2. Northern blot analysis of the various in vivo-selected cell populations revealed expression patterns for these genes that correlated with metastatic behavior. SPARC, IL13R 2, VCAM1 and MMP2 belong to the subset of genes whose expression is generally restricted to aggressive lung metastatic populations and are rarely expressed (less than 10% prevalence for VCAM1 and IL13R 2, and less than 2% prevalence for SPARC and MMP2) among randomly picked SCPs. In contrast, the expression of ID1, CXCL1, COX2, EREG, and MMP1 is not restricted to aggressive lung metastasis populations but increases with lung metastatic ability. Analysis of protein expression for these genes confirmed that the differences in mRNA levels translated into significant alterations in protein levels.

To determine if these genes play a causal role in lung metastasis, they were overexpressed via retroviral infection in the parental population either individually, in groups of three, or in groups of six. Cells overexpressing ID1, SPARC, IL13R 2, EREG or CXCL1 were modestly more active at forming lung metastasis when compared to cells infected with vector controls. Consistent with the hypothesis that metastasis requires the concerted action of multiple effectors, combinations of these genes invariably led to more aggressive metastatic activity and some combinations recapitulated the aggressiveness of the LM2 population. Triple combinations of lung metastasis genes in parental cells did not enhance bone metastatic activity, supporting their identity as tissue-specific mediators of metastasis. The necessity of some of these genes was tested by stably decreasing their expression in LM2 cells with short-hairpin RNAi vectors. Reduction of ID1, VCAM1, or IL13R 2 levels decreased the lung metastatic activity of LM2 cells by more than 10-fold. Collectively, the results show that these nine genes are not only markers but also functional mediators of lung-specific metastasis.

A biologically meaningful and clinically relevant gene profile that mediates lung metastasis should be uniquely expressed by a subgroup of patients that relapse to the lung and it should associate with clinical outcome. To test this, a cohort of 82 breast cancer patients treated at Memorial Sloan-Kettering Cancer Center (MSKCC) was used in a univariate Cox proportional hazards model to relate the expression level of each lung metastasis signature gene with clinical outcome. Twelve of the 54 genes are significantly associated with lung metastasis-free survival, including MMP1, CXCL1, and PTGS2 as reflected in Table 5.

TABLE 5

| Probe set | Gene Symbol | Hazard Ratio | Lower 95% | Upper 95% | p-value |
|---|---|---|---|---|---|
| 204070_at | RARRES3 | 0.434 | 0.291 | 0.648 | 0.00001 |
| 221009_s_at | ANGPTL4 | 2.991 | 1.661 | 5.388 | 0.00005 |
| 203571_s_at | C10orf116 | 0.608 | 0.467 | 0.792 | 0.00047 |
| 202728_s_at | LTBP1 | 3.364 | 1.467 | 7.711 | 0.00074 |
| 205017_s_at | MBNL2 | 3.133 | 1.357 | 7.231 | 0.00169 |
| 201564_s_at | FSCN1 | 1.975 | 1.28 | 3.047 | 0.00201 |
| 201324_at | EMP1 | 2.997 | 1.411 | 6.369 | 0.00272 |
| 210340_s_at | CSF2RA | 1.805 | 1.212 | 2.687 | 0.00283 |
| 204475_at | MMP1 | 1.313 | 1.064 | 1.619 | 0.00742 |
| 212942_s_at | KIAA1199 | 1.617 | 1.076 | 2.431 | 0.02083 |
| 204470_at | CXCL1 | 1.356 | 1.076 | 1.708 | 0.02191 |
| 204748_at | PTGS2 | 1.451 | 1.03 | 2.043 | 0.02628 |
| 202986_at | ARNT2 | 0.746 | 0.542 | 1.026 | 0.06494 |
| 213067_at | MYH10 | 0.674 | 0.429 | 1.06 | 0.06899 |
| 213075_at | OLFML2A | 0.434 | 0.165 | 1.139 | 0.07305 |
| 222182_s_at | CNOT2 | 0.365 | 0.12 | 1.108 | 0.07775 |
| 206785_s_at | KLRC1 | 0.752 | 0.544 | 1.04 | 0.08261 |
| 208161_s_at | ABCC3 | 0.776 | 0.574 | 1.048 | 0.10283 |
| 202145_at | LY6E | 0.704 | 0.437 | 1.136 | 0.13893 |
| 202017_at | EPHX1 | 0.678 | 0.387 | 1.186 | 0.17169 |
| 209505_at | NR2F1 | 0.806 | 0.579 | 1.121 | 0.21238 |
| 210663_s_at | KYNU | 1.235 | 0.887 | 1.718 | 0.21883 |
| 210136_at | MBP | 1.431 | 0.809 | 2.532 | 0.22674 |
| 219959_at | MOCOS | 1.359 | 0.83 | 2.226 | 0.23861 |
| 201061_s_at | STOM | 0.613 | 0.267 | 1.408 | 0.24098 |
| 213428_s_at | COL6A1 | 1.542 | 0.722 | 3.293 | 0.25386 |
| 219563_at | C14orf39 | 0.657 | 0.319 | 1.355 | 0.25881 |
| 220217_x_at | SPANXC | 0.773 | 0.474 | 1.261 | 0.28465 |
| 213537_at | HLA-DPA1 | 0.786 | 0.493 | 1.253 | 0.3343 |
| 213711_at | KRTHB1 | 1.1 | 0.899 | 1.347 | 0.36209 |
| 201645_at | TNC | 1.195 | 0.805 | 1.772 | 0.37407 |
| 201721_s_at | LAPTM5 | 1.305 | 0.634 | 2.687 | 0.48354 |
| 201842_s_at | EFEMP1 | 0.865 | 0.57 | 1.313 | 0.49742 |
| 213194_at | ROBO1 | 1.216 | 0.699 | 2.113 | 0.49865 |
| 214040_s_at | GSN | 1.167 | 0.717 | 1.901 | 0.51734 |
| 220921_at | SPANXB1 | 0.892 | 0.612 | 1.301 | 0.54461 |
| 209030_s_at | IGSF4 | 0.755 | 0.3 | 1.899 | 0.54672 |
| 202350_s_at | MATN2 | 0.907 | 0.658 | 1.252 | 0.55728 |
| 208937_s_at | ID1 | 1.156 | 0.716 | 1.866 | 0.56958 |
| 209394_at | ASMTL | 0.816 | 0.4 | 1.667 | 0.58735 |
| 221760_at | MAN1A1 | 0.89 | 0.522 | 1.519 | 0.6692 |
| 205767_at | EREG | 1.058 | 0.814 | 1.374 | 0.67603 |
| 206172_at | IL13RA2 | 1.061 | 0.691 | 1.629 | 0.78848 |
| 211368_s_at | CASP1 | 1.065 | 0.663 | 1.71 | 0.79193 |

TABLE 5-continued

| Probe set | Gene Symbol | Hazard Ratio | Lower 95% | Upper 95% | p-value |
|---|---|---|---|---|---|
| 201069_at | MMP2 | 1.079 | 0.592 | 1.966 | 0.80346 |
| 203868_s_at | VCAM1 | 1.065 | 0.576 | 1.969 | 0.83993 |
| 204698_at | ISG20 | 0.973 | 0.743 | 1.273 | 0.84223 |
| 205623_at | ALDH3A1 | 0.957 | 0.598 | 1.531 | 0.85511 |
| 201416_at | SOX4 | 0.941 | 0.462 | 1.913 | 0.86571 |
| 214827_at | PARD6B | 0.972 | 0.648 | 1.458 | 0.88897 |
| 217028_at | CXCR4 | 0.953 | 0.482 | 1.884 | 0.88906 |
| 221902_at | GPR153 | 0.964 | 0.524 | 1.773 | 0.90587 |
| 212667_at | SPARC | 0.969 | 0.489 | 1.922 | 0.92818 |
| 202149_at | NEDD9 | 1.033 | 0.51 | 2.092 | 0.92853 |

A cross-validated multivariate analysis using a linear combination of each of the 54 genes weighted by the univariate results distinguished patients divided into a high or a low risk group for developing lung metastasis (10 year lung metastasis-free survival of 56% vs 89%, p=0.0018;) but not bone metastasis (70% vs 79%, p=0.31). When a similar multivariate analysis was performed by weighting each gene by a t-statistic derived from comparing its expression between the LM2 cell lines with the parental MDA-MD-231 cells, the 54 genes again distinguished patients at high risk for developing lung metastasis (62% vs 88%, p=0.01) but not bone metastasis (75% vs 79%, p=0.49). These results indicate that a clinically relevant subgroup of patients express certain combinations of lung metastasis signature genes.

To directly determine the extent to which breast cancers express the lung metastasis signature in a manner resembling the LM2 cell lines, the 54-genes were used to hierarchically cluster the MSKCC data set. Manual inspection of branches in the dendrogram revealed a group of primary tumors that concordantly expressed many elements of this signature. In particular, a subgroup of primary tumors expressed to varying degrees a majority of the nine genes that were functionally validated. Interestingly, many patients that developed lung metastasis were among this group. Tumors in this group predominantly expressed markers of clinically aggressive disease including estrogen receptor/progesterone receptor negativity, a Rosetta-type poor-prognosis signature, and a basal cell subtype of breast cancer. There was no association of our signature with high HER2 expression. A molecularly similar subgroup of breast cancer was identified when the clustering analysis was repeated on a previously published Rosetta microarray data set of 78 breast cancer patients, suggesting that the findings are not unique to our cohort of patients.

Although the results of the hierarchical clustering are suggestive, this approach can lead to arbitrary class assignments and is generally not ideal for class prediction. Therefore, we took advantage of the repeated observation of our signature in two independent data sets. For training purposes the Rosetta data set was used to define a group of patients expressing the lung metastasis signature most resembling the LM2 cell lines. All 48 out of the 54 lung metastasis genes that were shared between the MSKCC and Rosetta data set microarray platforms were subsequently utilized to generate a classifier to distinguish these tumors from the remaining tumors in the cohort (Table 6).

TABLE 6

| p-value | UG cluster | Gene symbol | Description |
|---|---|---|---|
| <0.000001 | Hs.118400 | FSCN1 | Fascin homolog 1, actin-bundling protein (*Strongylocentrotus purpuratus*) |
| <0.000001 | Hs.83169 | MMP1 | Matrix metalloproteinase 1 (interstitial collagenase) |
| <0.000001 | Hs.9613 | ANGPTL4 | Angiopoietin-like 4 |
| 0.000006 | Hs.74120 | C10orf116 | Chromosome 10 open reading frame 116 |
| 0.00002 | Hs.789 | CXCL1 | Chemokine (C-X-C motif) ligand 1 (melanoma growth stimulating activity, alpha) |
| 0.000355 | Hs.196384 | PTGS2 | Prostaglandin-endoperoxide synthase 2 (prostaglandin G/H synthase and cyclooxygenase) |
| 0.000444 | Hs.185568 | KRTHB1 | Keratin, hair, basic, 1 |
| 0.000506 | Hs.109225 | VCAM1 | Vascular cell adhesion molecule 1 |
| 0.000627 | Hs.17466 | RARRES3 | Retinoic acid receptor responder (tazarotene induced) 3 |
| 0.001263 | Hs.368256 | LTBP1 | Latent transforming growth factor beta binding protein 1 |
| 0.004365 | Hs.444471 | KYNU | Kynureninase (L-kynurenine hydrolase) |
| 0.005179 | Hs.421986 | CXCR4 | Chemokine (C-X-C motif) receptor 4 |
| 0.006426 | Hs.77667 | LY6E | Lymphocyte antigen 6 complex, locus E |
| 0.007153 | Hs.410900 | ID1 | Inhibitor of DNA binding 1, dominant negative helix-loop-helix protein |
| 0.010871 | Hs.255149 | MAN1A1 | Mannosidase, alpha, class 1A, member 1 |
| 0.032361 | Hs.388589 | NEDD9 | Neural precursor cell expressed, developmentally down-regulated 9 |
| 0.03713 | Hs.115263 | EREG | Epiregulin |
| 0.046859 | Hs.98998 | TNC | Tenascin C (hexabrachion) |
| 0.053773 | Hs.357901 | SOX4 | SRY (sex determining region Y)-box 4 |
| 0.05492 | Hs.157986 | MOCOS | Molybdenum cofactor sulfurase |
| 0.062067 | Hs.165725 | CNOT2 | CCR4-NOT transcription complex, subunit 2 |
| 0.071707 | Hs.436200 | LAPTM5 | Lysosomal-associated multispanning membrane protein-5 |
| 0.079271 | Hs.153647 | MATN2 | Matrilin 2 |
| 0.080391 | Hs.156682 | IGSF4 | Immunoglobulin superfamily, member 4 |
| 0.096189 | Hs.306692 | EMP1 | Epithelial membrane protein 1 |
| 0.097858 | Hs.105434 | ISG20 | Interferon stimulated gene 20 kDa |
| 0.119096 | Hs.280311 | MYH10 | Myosin, heavy polypeptide 10, non-muscle |
| 0.124785 | Hs.301198 | ROBO1 | Roundabout, axon guidance receptor, homolog 1 (*Drosophila*) |
| 0.213167 | Hs.361748 | NR2F1 | Nuclear receptor subfamily 2, group F, member 1 |
| 0.230817 | Hs.125715 | MBNL2 | Muscleblind-like 2 (*Drosophila*) |
| 0.25087 | Hs.367877 | MMP2 | MMP2 |
| 0.254227 | Hs.446537 | GSN | Gelsolin (amyloidosis, Finnish type) |

TABLE 6-continued

| p-value | UG cluster | Gene symbol | Description |
|---|---|---|---|
| 0.255766 | Hs.531581 | GPR153 | G protein-coupled receptor 153 |
| 0.274128 | Hs.336046 | IL13RA2 | Interleukin 13 receptor, alpha 2 |
| 0.345846 | Hs.357004 | OLFML2A | Olfactomedin-like 2A |
| 0.36839 | Hs.6111 | ARNT2 | Aryl-hydrocarbon receptor nuclear translocator 2 |
| 0.423864 | Hs.111779 | SPARC | Secreted protein, acidic, cysteine-rich (osteonectin) |
| 0.507582 | Hs.2490 | CASP1 | Caspase 1, apoptosis-related cysteine protease (interleukin 1, beta, convertase) |
| 0.650845 | Hs.76224 | EFEMP1 | EGF-containing fibulin-like extracellular matrix protein 1 |
| 0.75516 | Hs.520937 | CSF2RA | Colony stimulating factor 2 receptor, alpha, low-affinity (granulocyte-macrophage) |
| 0.764736 | Hs.439776 | STOM | Stomatin |
| 0.830009 | Hs.512576 | KLRC1 | Killer cell lectin-like receptor subfamily C, member 1 |
| 0.830451 | Hs.415997 | COL6A1 | Collagen, type VI, alpha 1 |
| 0.843369 | Hs.458420 | ASMTL | Acetylserotonin O-methyltransferase-like |
| 0.846476 | Hs.575 | ALDH3A1 | Aldehyde dehydrogenase 3 family, memberA1 |
| 0.867387 | Hs.89649 | EPHX1 | Epoxide hydrolase 1, microsomal (xenobiotic) |
| 0.899238 | Hs.90786 | ABCC3 | ATP-binding cassette, sub-family C (CFTR/MRP), member 3 |
| 0.926966 | Hs.914 | HLA-DPA1 | Major histocompatibility complex, class II, DP alpha 1 |

This classifier was then applied to the MSKCC cohort to identify tumors that express the lung metastasis signature in a manner resembling the LM2 cell lines. These patients had a markedly worse lung metastasis-free survival but not bone metastasis-free survival. These results were independent of ER status and classification as a Rosetta-type poor prognosis tumor. Six of the nine genes that we tested in functional validation studies (MMP1, CXCL1, PTGS2, ID1, VCAM1, and EREG) were among the 18 most univariately significant (p<0.05) genes that distinguished the patients used to train the classifier, and classification using only these 18 genes gave similar results. The three remaining genes (SPARC, IL13RA2, MMP2) are members of the lung metastasis virulence subset and were expressed only in the most highly metastatic cell lines in our model system.

FIGS. 3 A-D illustrate the ability of a 54 gene signature to identify breast cancer patients at high risk for developing lung but not bone metastasis. Kaplan-Meier survival curves for lung metastasis-free survival and bone metastasis-free survival of patients in the MSKCC cohort and the results are shown in FIGS. 3A and B. The lower line represents tumors that express the lung metastasis signature based on the classifier trained on the Rosetta primary breast tumor cohort. The upper line represents all remaining tumors in the cohort. The p-value for each survival curve is shown. FIGS. 3C and D show survival analysis for lung metastasis restricted to ER-negative tumors or Rosetta-type poor prognosis tumors. In each case, the ability to distinguish between risk of lung metastasis is clear.

To assess the utility of targeting lung metastasis genes for therapeutic purposes, we generated RNAi vectors that potently decrease the expression levels of 4 lung metastasis mediators: MMP1, MMP2, PTGS2, and Epiregulin. These RNAi vectors were introduced into highly lung metastatic cells (LM2) either individually or in combination, and effects on lung metastatic aggressiveness were quantified using bioluminescence imaging. We observed that individual genetic targeting of any of these four genes, as well as dual targeting of both matrix metalloproteinases, did not significantly inhibit the rate of lung metastasis formation (FIG. 1A). However, combinations inhibiting epiregulin expression, as well as triple inhibition of MMP1, MMP2, and PTGS2, revealed synergistic and essential roles for these genes in promoting lung metastasis (FIG. 1B). To test whether these genes also contributed to the aggressive primary tumorigenicity exhibited by these LM2 cells, we injected the various knockdown cell lines orthotopically into the mouse mammary fat pad. Primary tumor growth curves established an essential role for the synergistic activities of epiregulin, MMP1, MMP2, and PTGS2 in aggressive primary tumorigenicity (FIG. 1C), which is an established marker of poor prognosis is breast cancer.

Figure 2A:
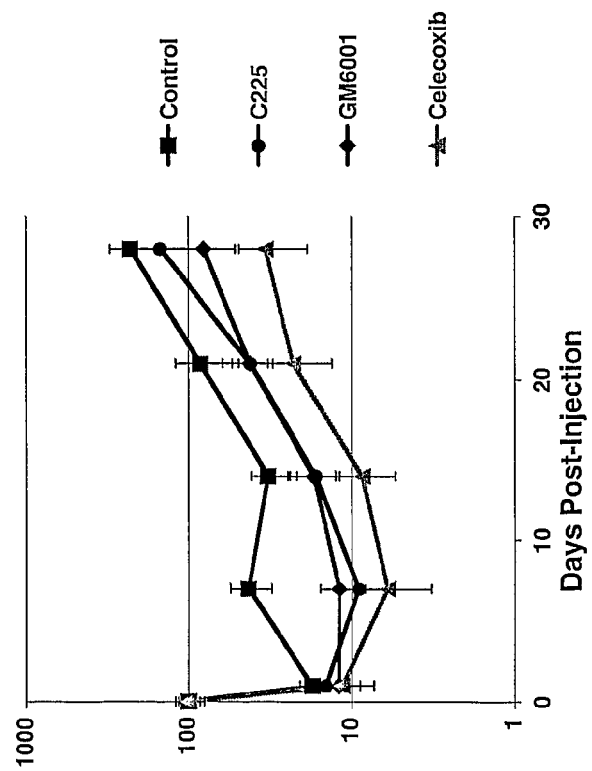
Figure 3A:
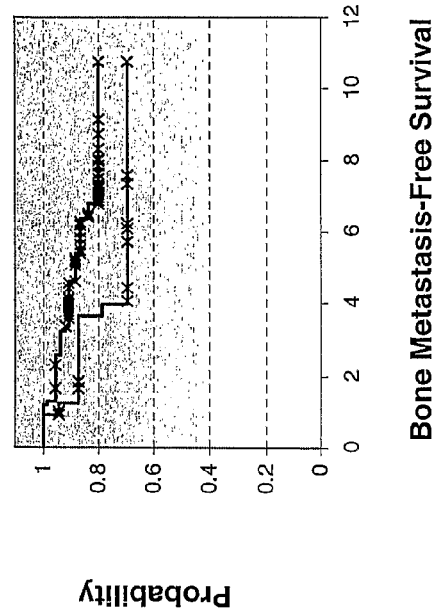
FIGS. 3A-B show the ability to identify patients at higher risk of lung metastasis using the invention.
Figure 3B:
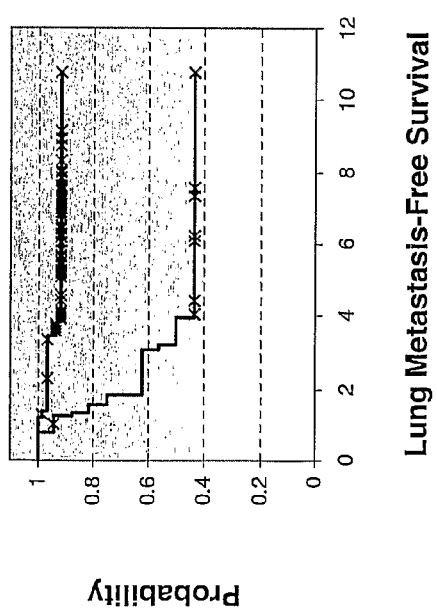
Figure 3C:
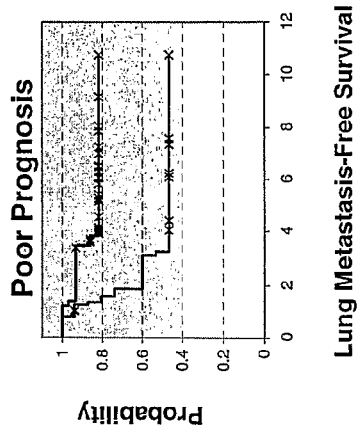
Figure 3D:
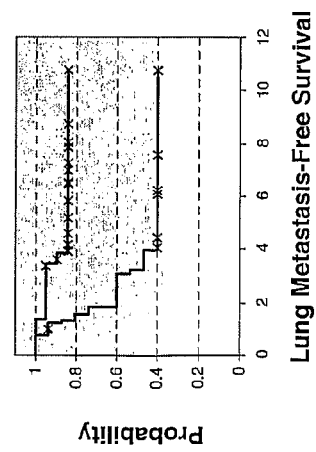

Experiments were also performed to test the efficacy of combined pharmacological targeting of these same lung metastasis mediators. Preliminary results using Erbitux (anti-EGFR antibody to target the epiregulin pathway), Celecoxib (PTGS2-selective inhibitor), and GM-6001 (Ilomastat, an experimental broad-spectrum MMP inhibitor) yielded findings similar to those obtained using genetic knockdowns. In particular, combinations of inhibitors were synergistically more potent in preventing lung metastasis than any of the drugs administered individually (FIGS. 2A and 2B).

Experimental Procedures

Cell lines. The parental MDA-MB-231 cell line was obtained from the American Type Tissue Collection. Its derivative cell lines and SCPs were previously described. (Kang (2003), supra) Cells were grown in high-glucose Dulbecco's modified Eagles medium with 10% fetal bovine serum. For bioluminescent tracking, cell lines were retrovirally infected with a triple fusion protein reporter construct encoding herpes simplex virus thymidine kinase 1, green fluorescent protein (GFP) and firefly luciferase 13, 33, 34. GFP-positive cells were enriched by fluorescence-activated cell sorting.

Animal studies. All animal work was done in accordance with an IACUC approved protocol. Four to 6-week-old Balb/c nude mice (NCI) were used for all xenografting studies. For lung metastasis formation, $2 \times 10^5$ viable cells were washed and harvested in PBS and subsequently injected into the lateral tail vein in a volume of 0.1 mL. Endpoint assays were conducted at 15 weeks post-injection unless significant morbidity required that the mouse be sacrificed earlier. For bone metastasis, $1 \times 10^5$ cells in PBS were injected into the left ventricle of anesthetized mice (100 mg/kg Ketamine; 10 mg/kg Xylazine). Mice were imaged for luciferase activity immediately after injection to exclude any that were not successfully xenografted.

For mammary fat pad tumor assays, cells were harvested by trypsinization, washed twice in PBS and counted. Cells were then resuspended ($1 \times 10^7$ cells/ml) in a 50:50 solution of PBS and Matrigel. Mice were anesthetized, a small incision was made to visualize the mammary gland and $1 \times 10^6$ cells were injected directly into the mammary fatpad. The incision was closed with wound clips and primary tumor outgrowth was monitored weekly by taking measurements of the tumor length (L) and width (W). Tumor volume was calculated as per $4/3 \times L/2(W/2)$. For metastasis assays, tumors were surgically resected when they reached a tumor volume greater than 300 mm. After resection, the mice were monitored by bioluminescent imaging for the development of metastases.

Bioluminescent imaging and analysis. Mice were anesthetized and retro-orbitally injected with 1.5 mg of D-luciferin (15 mg/mL in PBS). Imaging was completed between 2-5 minutes post-injection using a Xenogen IVIS system coupled to Living Image acquisition and analysis software (Xenogen). For BLI plots, photon flux was calculated for each mouse using a rectangular region of interest (ROI) encompassing the thorax of the mouse in a prone position. This value was scaled to a comparable background value (from a luciferin-injected mouse with no tumor cells), and then normalized to the value obtained immediately post-xenografting (day 0), so that all mice had an arbitrary starting BLI signal of 100.

Lung histology. Lungs were harvested at necropsy. For hematoxylin and eosin staining, lungs were fixed in 10% neutral buffered formalin overnight, washed with PBS and dehydrated in 70% ethanol before paraffin embedding (Histoserv). For CD31 staining, lungs were fixed in 4% paraformaldehyde overnight and treated with 30% sucrose for 12-24 h before cryosectioning. Staining was performed using anti-CD31 antibody (sc-1506, Santa Cruz Biotechnology).

RNA isolation, labeling and microarray hybridization. Methods for RNA extraction, labeling, and hybridization for DNA microarray analysis of the cell lines have been previously described 4. For the primary breast tumor data, tissues from primary breast cancers were obtained from therapeutic procedures performed as part of routine clinical management. Samples were snap frozen in liquid nitrogen and stored at $-80°$ C. Each sample was examined histologically using hematoxylin and eosin stained cryostat sections. Regions were manually dissected from the frozen block to provide consistent tumor cell content of greater than 70% in tissues used for analysis. All studies were conducted under MSKCC Institutional Review Board approved protocols. RNA was extracted from frozen tissues by homogenization in TRIzol reagent (GIBCO/BRL) and evaluated for integrity. Complementary DNA was synthesized from total RNA using a T7-promoter-tagged-dT primer. RNA target was synthesized by in vitro transcription and labeled with biotinylated nucleotides (Enzo Biochem, Farmingdale, N.Y.). Labeled target was assessed by hybridization to Test3 arrays (Affymetrix, Santa Clara, Calif.). All gene expression analysis was carried out using HG-U133A GeneChip. Gene expression was quantitated using MAS 5.0 or GCOS (Affymetrix).

Analysis of mRNA and protein expression. Total RNA from subconfluent MDA-MB-231 cells were harvested using the RNeasy kit (Qiagen). Samples were electrophoresed in MOPS buffer and transferred to a Hybond N+ membrane (Amersham). Radioactive probes for Northern blotting were derived from fragments of the relevant cDNA, and hybridization was done at $68°$ C. for 3 h.

For immunoblotting, cells were washed with PBS and lysed in RIPA buffer (50 mM Tris-HCl pH 7.4, 1% NP-40, 0.25% Na-deoxycholate, 150 mM NaCl, 1 mM EDTA) supplemented with 50 mM NaF, 20 mM-glycerophosphate, and complete protease inhibitor cocktail (Roche). Proteins were separated by SDS-PAGE, and transferred to PVDF membranes that were immunoblotted with antibodies against ID1 or VCAM1 (Santa Cruz Biotechnology), SPARC (R&D Systems), and -tubulin (Sigma). Secreted MMP-1, MMP-2 and CXCL1 were analyzed in conditioned media using commercially available ELISA kits (R&D Systems). Cells were plated in triplicate at 90% confluency in 6 well plates, and conditioned media was collected 48 h later. Media was cleared of cells by centrifuging at 2000 rpm for 5 min, and subsequently assayed for protein concentration according to the protocols for the relevant ELISA kits.

Cell-surface IL13R 2 and VCAM1 were analyzed by flow cytometry in cells harvested with trypsin-EDTA and washed twice with cold PBS. CyChrome-conjugated anti-human VCAM1 (BD Pharmingen), phycoerythrin-conjugated anti-human IL13R 2 (Cell Sciences), or control IgG were incubated in FACS buffer (0.1% sodium azide and 1% bovine serum albumin in PBS) at concentrations recommended by the supplier, for 1 h at $4°$ C. in the dark. Cells were washed twice and re-suspended in cold FACS buffer. Flow cytometry data was collected on a FACScalibur (BD) instrument and analyzed using FlowJo software.

Overexpression and knockdown constructs. For overexpression studies, human cDNAs of interest were cloned into pBabe-puro and/or pBabe-hygro retroviral expression vectors. For single transductions, 20 μg of DNA were transfected into the amphotropic GPG29 packaging cell line using Lipofectamine 2000 (Invitrogen) at a ratio of 1:3 (μg DNA:μl Lipofectamine 2000). Virus-containing supernatants were harvested daily between 48 and 96 h post-transfection. Media was centrifuged at 2000 rpm for 5 minutes and subsequently cleared of remnant cells using a 0.45 μm syringe filter (VWR). Filtered viral media was added to 70% confluent MDA-MB-231 cells in the presence of 8 μg/ml polybrene (Sigma), and incubated overnight. 72 h post-infection, cell populations were treated with either puromycin (Sigma) or hygromycin (Calbiochem). Expression of the relevant transgenes was validated by Northern blot or protein expression analysis.

For combination overexpression experiments, groups of three genes expressing the same drug resistance marker were co-transfected into GPG29 packaging cells as described, but using 15 micrograms of each plasmid. Viral harvesting and infection was identical to that described above. Sextet transductions were generated as two sequential triple infections. Cells were selected for the first drug resistance marker before being infected and selected for the second resistance marker. The SPARC, ID1, and MMP1 triplet encoded a puromycin-resistance marker, whereas the VCAM1, IL13RA2, and MMP2 as well as the CXCL1, EREG, and COX2 triplets delivered hygromycin-resistant markers into the recipient cells.

For knockdown experiments, short hairpin RNAi constructs were cloned into the pRetroSuper plasmid according to previously published protocols. Retroviral infection into LM2 cells was achieved as described above for the overexpression constructs. Multiple hairpin constructs were screened for effective knockdown of the gene product of interest. 19 nucleotide target sequences that resulted in productive knockdown included: 5'-ggatcttgtgatctaaatc-3' (SPARC) (SEQ ID NO: 1), 5'-gaggaattacgtgctctgt-3' (ID1) (SEQ ID NO: 2), and 5'-ggtgaagacctatcgaaga-3' (IL13RA2) (SEQ ID NO: 3). For knockdown of VCAM1, LM2 cells were sequentially infected and puromycin-selected with two different pRetroSuper targeting constructs, encoding 5'-ggcagagtacgcaaacact-3' (SEQ ID NO: 4) and 5'-gtccctggaaaccaagagt-3' (SEQ ID NO: 5), respectively. Negative control cell lines were generated by infecting with a pRetroSuper construct targeting 5'-cggctgttactcacgcctc-3' (SEQ ID NO: 6), a sequence in the ID1 cDNA that did not yield any appreciable knockdown of the protein product by Western blotting.

Statistical analysis. The Kaplan-Meier method was used to estimate survival curves and the log-rank test was used to test for differences between curves. Analyses were performed using WinSTAT (R. Fitch Software). The site of distant metastasis for the patients in the MSKCC data set was determined from patient records. Lung metastasis as the site of first recurrence included patients that developed metastasis as the only site of recurrence or patients that developed lung metastasis concurrently with or within months of metastasis to other sites.

Genetic knockdown of MMP1, MMP2, and PTGS2 was also achieved using pRetroSuper technology, targeting the following 19 nt sequences: 5'-agcggagaaatagtggccc-3' (MMP1) (SEQ ID NO: 7), 5'-ggacggactcctggctcat-3' (MMP2) (SEQ ID NO: 8), and 5'-gggctgtccctttacttca-3' (PTGS2) (SEQ ID NO: 9). For EREG targeting, an alternative gene-targeting vector was used (pSHAG), which expresses the short hairpin under a U6 promoter and contains stabilizing microRNA sequences. The two target sequences in the EREG gene that were utilized were: 5'-cccaatatattctgaccgttaa-3' ((SEQ ID NO: 10) and 5'-accacaaatgcataaatgcata-3' (SEQ ID NO: 11). Retroviral production and LM2 infections were performed as described above.

The invention claimed is:

1. A method for evaluating breast cancer tissue derived from a patient, comprising the steps of:
   (a) obtaining a sample of breast cancer tissue from the patient,
   (b) evaluating the sample of breast cancer tissues to determine expression levels of plurality of genes selected from the group consisting of SPARC, IL13RA2, KLRC1 and KLRC2, MMP1, KYNU, EREG, TNC, ISG20, ALDH3A1, KRTHB1, PTGS2, LAPTM5, C10orf116, ROBO1, SPANXC, ANGPTL4, FSCN1, SOX4, SPANXB1 and SPANXC, COL6A1, CXCL1, MMP2, STOM, GPR153, MAN1A1, C14orf139, CASP1, IGSF4, LTBP1, NR2F1, EMP1, ID1, CNOT2, VCAM1, OLFML2A, NEDD9, CSF2RA, MOCOS, EPHX1, MBNL2, LOC388483, GSN, MYH10, ARNT2, RARRES3, EFEMP1, MATN2, LY6E, HLA-DPA1, ASMTL, ABCC3, KIAA1199, CXCR4, and PARD6B to obtain a sample signature for the cancer tissue sample, wherein the evaluation is performed by a method selected from the group consisting of binding of complementary oligonucleotide probes, RT-PCR, nucleic acid microarray analysis, binding of RNA specific antibodies, protein-ligand binding assays, protein immunoassays and protein microarray assays, and
   (c) comparing the sample signature to a reference signature, wherein the reference signature defines a standard expression level for each gene and a significant change direction for each gene,
   wherein the significant change direction is upregulation if the gene is SPARC, IL13RA2, KLRC1 and KLRC2, MMP1, KYNU, EREG, TNC, ISG20, ALDH3A1, KRTHB1, PTGS2, LAPTM5, C10orf116, ROBO1, SPANXC, ANGPTL4, FSCN1, SOX4, SPANXB1 and SPANXC, COL6A1, CXCL1, MMP2, STOM, GPR153, MAN1A1, C14orf139, CASP1, IGSF4, LTBP1, NR2F1, EMP1, ID1, CNOT2, or VCAM1 and downregulation if the gene is OLFML2A, NEDD9, CSF2RA, MOCOS, EPHX1, MBNL2, LOC388483, GSN, MYH10, ARNT2, RARRES3, EFEMP1, MATN2, LY6E, HLA-DPA1, ASMTL, ABCC3, KIAA1199, CXCR4, or PARD6B, and
   wherein a difference in the expression level in the sample signature that differs from the reference signature level for the gene in the significant change direction for the gene for at least a predetermined number of the genes tested is indicative that the patient has an increased risk of lung metastasis of the breast cancer.

2. The method of claim 1, wherein the plurality of genes includes the genes FSCN1, MMP1, ANGPTL4, C10orf116, CXCL1, PTGS2, KRTHB1, VCAM1, RARRES3, LTBP1, KYNU, CXCR4, LY6E, ID1, MAN1A1, NEDD9, and EREG.

3. The method of claim 2, wherein the plurality of genes further includes the gene TNC.

4. The method of claim 2, wherein the predetermined number is 10.

5. The method of claim 2, wherein the predetermined number is 15.

6. The method of claim 3, wherein the predetermined number is 10.

7. The method of claim 3, wherein the predetermined number is 15.

8. A method for treating breast cancer in a patient to reduce the risk of lung cancer metastasis, comprising the steps of:
   evaluating breast cancer tissue derived from a patient by a method comprising the steps of:
   (a) obtaining a sample of breast cancer tissue from the patient,
   (b) evaluating the sample of breast cancer tissues to determine expression levels of plurality of genes selected from the group consisting of SPARC, IL13RA2, KLRC1 and KLRC2, MMP1, KYNU, EREG, TNC, ISG20, ALDH3A1, KRTHB1, PTGS2, LAPTM5, C10orf116, ROBO1, SPANXC, ANGPTL4, FSCN1, SOX4, SPANXB1 and SPANXC, COL6A1, CXCL1, MMP2, STOM, GPR153, MAN1A1, C14orf139, CASP1, IGSF4, LTBP1, NR2F1, EMP1, ID1, CNOT2, VCAM1, OLFML2A, NEDD9, CSF2RA, MOCOS, EPHX1, MBNL2, LOC388483, GSN, MYH10, ARNT2, RARRES3, EFEMP1, MATN2, LY6E, HLA-DPA1, ASMTL, ABCC3, KIAA1199, CXCR4, and PARD6B to obtain a sample signature for the cancer tissue sample, and
   (c) comparing the sample signature to a reference signature, wherein the reference signature defines a standard expression level for each gene and a significant change direction for each gene,
   wherein the significant change direction is upregulation if the gene is SPARC, IL13RA2, KLRC1 and KLRC2, MMP1, KYNU, EREG, TNC, ISG20, ALDH3A1, KRTHB1, PTGS2, LAPTM5, C10orf116, ROBO1, SPANXC, ANGPTL4, FSCN1, SOX4, SPANXB1 and SPANXC, COL6A1, CXCL1, MMP2, STOM, GPR153, MAN1A1, C14orf139, CASP1, IGSF4, LTBP1, NR2F1, EMP1, ID1, CNOT2, or VCAM1 and downregulation if the gene is OLFML2A, NEDD9, CSF2RA, MOCOS, EPHX1, MBNL2, LOC388483, GSN, MYH10, ARNT2, RARRES3, EFEMP1, MATN2, LY6E, HLA-DPA1, ASMTL, ABCC3, KIAA1199, CR4, or PARD6B, and
   wherein a difference in the expression level in the sample signature that differs from the reference signature level for the gene in the significant change direction for the gene for at least a predetermined number of the genes tested is indicative that the patient has an increased risk of lung metastasis of the breast cancer, and
   if the evaluation indicates an increased risk of lung metastasis, treating the patient to reduce the risk of lung cancer metastasis with a therapeutic combination comprising at least two agents, wherein the agents are inhibitors of a protein selected from the group consisting of SPARC, IL13Rα2, VCAM1, MMP1, MMP2, ID1, CXCL1, PTSG2 and EREG.

9. The method of claim 8, wherein the therapeutic combination comprises a first agent effective to inhibit epiregulin activity and a second agent effective to inhibit activity of a protein selected from the group consisting of MMP1, MMP2 and PTGS2.

10. The method of claim 9, wherein the first agent is an oligonucleotide.

11. The method of claim 9, wherein the second agent is an oligonucleotide.

12. The method of claim 9, wherein the first agent is a small molecule inhibitor.

13. The method of claim 9, wherein the first agent is selected from the group consisting of Erbitux, Iressa and Tarceva.

14. The method of claim 8, wherein the therapeutic combination comprises at least three agents that are inhibitors of a protein selected from the group consisting of SPARC, IL13Rα2, VCAM1, MMP1, MMP2, ID1, CXCL1, PTSG2 and EREG.

15. The method of claim 14, wherein the therapeutic combination comprises agents effective to inhibit activity of MMP1, MMP2 and PTGS2.

16. The method of claim 15, wherein the therapeutic combination comprises a small molecule inhibitor of PTGS2 activity.

17. The method of claim 14, wherein the therapeutic combination comprises oligonucleotide agents effective to inhibit activity of MMPI and MMP2.

18. The method of claim 17, wherein the oligonucleotide agents are Seq ID No. 7 and seq ID No. 8.

* * * * *

UNITED STATES PATENT AND TRADEMARK OFFICE
CERTIFICATE OF CORRECTION

| | |
|---|---|
| PATENT NO. | : 8,906,606 B2 |
| APPLICATION NO. | : 13/447684 |
| DATED | : December 9, 2014 |
| INVENTOR(S) | : Gupta et al. |

Page 1 of 1

It is certified that error appears in the above-identified patent and that said Letters Patent is hereby corrected as shown below:

In the Claims

Column 31, Claim 17, Line 12 should read: … activity of MMP1 and MMP2.

Signed and Sealed this
Twenty-first Day of April, 2015

Michelle K. Lee
*Director of the United States Patent and Trademark Office*

SEQUENCE LISTING

```
<160> NUMBER OF SEQ ID NOS: 11

<210> SEQ ID NO 1
<211> LENGTH: 19
<212> TYPE: DNA
<213> ORGANISM: artificial
<220> FEATURE:
<223> OTHER INFORMATION: RNAi target sequence for SPARC

<400> SEQUENCE: 1
ggatcttgtg atctaaatc                                                     19

<210> SEQ ID NO 2
<211> LENGTH: 19
<212> TYPE: DNA
<213> ORGANISM: artificial
<220> FEATURE:
<223> OTHER INFORMATION: RNAi target sequence for ID1

<400> SEQUENCE: 2
gaggaattac gtgctctgt                                                     19

<210> SEQ ID NO 3
<211> LENGTH: 19
<212> TYPE: DNA
<213> ORGANISM: artificial
<220> FEATURE:
<223> OTHER INFORMATION: RNAi target sequenced for IL13RA2

<400> SEQUENCE: 3
ggtgaagacc tatcgaaga                                                     19

<210> SEQ ID NO 4
<211> LENGTH: 19
<212> TYPE: DNA
<213> ORGANISM: artificial
<220> FEATURE:
<223> OTHER INFORMATION: RNAi target sequence for VCAM1

<400> SEQUENCE: 4
ggcagagtac gcaaacact                                                     19

<210> SEQ ID NO 5
<211> LENGTH: 19
<212> TYPE: DNA
<213> ORGANISM: artificial
<220> FEATURE:
<223> OTHER INFORMATION: RNAi target sequence for VCAM1

<400> SEQUENCE: 5
gtccctggaa accaagagt                                                     19
```

```
<210> SEQ ID NO 6
<211> LENGTH: 19
<212> TYPE: DNA
<213> ORGANISM: artificial
<220> FEATURE:
<223> OTHER INFORMATION: RNAi control sequence derived from ID1 cDNA

<400> SEQUENCE: 6
cggctgttac tcacgcctc                                              19

<210> SEQ ID NO 7
<211> LENGTH: 19
<212> TYPE: DNA
<213> ORGANISM: artificial
<220> FEATURE:
<223> OTHER INFORMATION: RNAi target sequence for MMP1

<400> SEQUENCE: 7
agcggagaaa tagtggccc                                              19

<210> SEQ ID NO 8
<211> LENGTH: 19
<212> TYPE: DNA
<213> ORGANISM: artificial
<220> FEATURE:
<223> OTHER INFORMATION: RNAi gtarget sequence for MMP2

<400> SEQUENCE: 8
ggacggactc ctggctcat                                              19

<210> SEQ ID NO 9
<211> LENGTH: 19
<212> TYPE: DNA
<213> ORGANISM: artificial
<220> FEATURE:
<223> OTHER INFORMATION: RNAi target sequence for PTGS2

<400> SEQUENCE: 9
gggctgtccc tttacttca                                              19

<210> SEQ ID NO 10
<211> LENGTH: 22
<212> TYPE: DNA
<213> ORGANISM: artificial
<220> FEATURE:
<223> OTHER INFORMATION: RNAi target sequence for EREG

<400> SEQUENCE: 10
cccaatatat tctgaccgtt aa                                          22

<210> SEQ ID NO 11
<211> LENGTH: 22
<212> TYPE: DNA
<213> ORGANISM: artificial
<220> FEATURE:
<223> OTHER INFORMATION: RNAi target sequence for EREG

<400> SEQUENCE: 11
accacaaatg cataaatgca ta                                          22
```